(12) United States Patent
Suez et al.

(10) Patent No.: US 10,377,720 B2
(45) Date of Patent: Aug. 13, 2019

(54) PROCESS FOR PREPARING A HYDROXYLAMINE PYRAZOLE COMPOUND

(71) Applicant: Adama Makhteshim Ltd., Beer-Sheva (IL)

(72) Inventors: Gal Suez, Beer-Sheva (IL); Michael Grabarnick, Meitar (IL); Alexander Frenklah, MaAle Adumim (IL); Heinz Steiner, Bubendorf (CH)

(73) Assignee: Adama Makhteshim Ltd., Beer-Sheva (IL)

( * ) Notice: Subject to any disclaimer, the term of this patent is extended or adjusted under 35 U.S.C. 154(b) by 0 days.

(21) Appl. No.: 15/573,850

(22) PCT Filed: May 9, 2016

(86) PCT No.: PCT/IL2016/050486
§ 371 (c)(1),
(2) Date: Nov. 14, 2017

(87) PCT Pub. No.: WO2016/181386
PCT Pub. Date: Nov. 17, 2016

(65) Prior Publication Data
US 2018/0258050 A1      Sep. 13, 2018

Related U.S. Application Data

(60) Provisional application No. 62/161,329, filed on May 14, 2015.

(51) Int. Cl.
C07D 231/22      (2006.01)
A01N 43/56       (2006.01)

(52) U.S. Cl.
CPC ............ *C07D 231/22* (2013.01); *A01N 43/56* (2013.01)

(58) Field of Classification Search
None
See application file for complete search history.

(56) References Cited

U.S. PATENT DOCUMENTS

| | | | | |
|---|---|---|---|---|
| 3,694,509 A | | 9/1972 | Rylander et al. | |
| 3,897,499 A | * | 7/1975 | Vollheim | B01J 23/40 502/167 |
| 3,927,101 A | * | 12/1975 | Le Ludec | 564/300 |
| 3,992,395 A | * | 11/1976 | Ludec | C07D 271/113 548/144 |
| 4,415,753 A | * | 11/1983 | Caskey | C07C 215/76 564/112 |
| 4,723,030 A | * | 2/1988 | Davis | C07C 239/18 560/19 |
| 2013/0178634 A1 | * | 7/2013 | Korte | C07D 231/22 548/371.1 |
| 2013/0338373 A1 | * | 12/2013 | Korte | C07D 231/22 548/371.1 |
| 2018/0230104 A1 | * | 8/2018 | Klauber | C07D 231/04 |

FOREIGN PATENT DOCUMENTS

| | | |
|---|---|---|
| EP | 0212375 | 3/1987 |
| WO | WO 99/12911 | 3/1999 |
| WO | WO 2012/038392 | 3/2012 |
| WO | WO 2012/120029 | 9/2012 |
| WO | WO 2016/181386 | 11/2016 |

OTHER PUBLICATIONS

JACS 36(6) 1170-1201 (1914) (Year: 1914).*
International Preliminary Report on Patentability dated Nov. 23, 2017 From the International Bureau of WIPO Re. Application No. PCT/IL2016/050486. (7 Pages).
International Search Report and the Written Opinion dated Jul. 6, 2016 From the International Searching Authority Re. Application No. PCT/IL2016/050486.

* cited by examiner

*Primary Examiner* — Nyeemah A Grazier

(57) ABSTRACT

A process for preparing, 2-[[[1-(4-chlorophenyl)-1H-pyrazol-3-yl]oxy]methyl]-N-hydroxy-benzenamine of formula (I) comprising: mixing 1-(4-chlorophenyl)-3-[(2-nitrophenyl)methoxy]-1H-pyrazole of formula (II) with a nitrogen-containing base, a sulfur compound, a solvent and a platinum-based catalyst in the presence of hydrogen.

18 Claims, No Drawings

PROCESS FOR PREPARING A HYDROXYLAMINE PYRAZOLE COMPOUND

RELATED APPLICATIONS

This application is a National Phase of PCT Patent Application No. PCT/IL2016/050486 having International filing date of May 9, 2016, which claims the benefit of priority under 35 USC § 119(e) of U.S. Provisional Patent Application No. 62/161,329 filed on May 14, 2015. The contents of the above applications are all incorporated by reference as if fully set forth herein in their entirety.

TECHNICAL FIELD

The present subject matter relates to a process for the selective preparation of a hydroxylamine pyrazole compound, more particularly for the selective preparation of 2-[[[1-(4-chlorophenyl)-1H-pyrazol-3-yl]oxy]methyl]-N-hydroxy-benzenamine.

BACKGROUND

The compound 2-[[[1-(4-chlorophenyl)-1H-pyrazol-3-yl]oxy]methyl]-N-hydroxy-benzenamine of the formula (I) is an important intermediate for preparing inter alia the fungicidal agents such as pyraclostrobin.

EP 0086363 describes a process for producing arylhydroxylamines in high yield with minimal formation of by-product arylamines.

WO 2012/120029 describes a process for the preparation of 2-[[[1-(4-chlorophenyl)-1H-pyrazol-3-yl]oxy]methyl]phenyl-hydroxylamine from the correspondingly substituted nitrobenzene compound by reacting the substituted nitrobenzene with hydrogen or hydrazine in the presence of a rhodium catalyst.

WO 1999/012911 describes a method for producing N-acylated (hetero)aromatic hydroxylamine derivatives by hydrogenating a (hetero)aromatic nitro-compound in the presence of a hydrogenation catalyst and in a mixture with an inert, aprotic solvent and an aliphatic amine.

The hydrogenation of nitro-aryl compounds to produce hydroxylamine compounds is not trivial as different side-products may possibly be formed, thereby reducing the yield of the desired hydroxylamine compounds.

According to Figueras, F.; Bernard, Coq. *J. Mol. Catal. A: Chem.* 2001, 173, 223-230, the selective semi-hydrogenation to a hydroxylamine compound is challenging because precious metal catalyst often reduce nitro compounds all the way to amine compounds. In addition, various other compounds can be formed as side-products. This includes a nitroso compound which is formed by hydrogenolysis of the nitro compound. Further hydrogenation of the nitroso compound gives a hydroxylamine compound. The catalytic hydrogenation of the hydroxylamine compound results in the formation of an amine compound. The first step for the formation of the azoxy compound is the condensation of the nitroso compound and the hydroxylamine compound. Further, the azoxy compound can be hydrogenated to an azo compound, which can be further hydrogenated to give a hydrazo compound. Another problem is that the hydroxylamine compound is unstable and can disproportionate to a nitroso compound, an amine compound and one molecule of water.

It would be highly desirable to have an improved process for the production of the compound of formula (I) which is suitable for industrial use, highly efficient, low-cost, environmentally friendly, and provides a high yield in a short reaction time, thereby overcoming the deficiencies of the prior art. The present subject matter provides such a process.

It is therefore a purpose of the present subject matter to provide a high-yield process for the preparation of 2-[[[1-(4-chlorophenyl)-1H-pyrazol-3-yl]oxy]methyl]-N-hydroxy-benzenamine with effective control of the reaction end point.

It is yet another purpose of the present subject matter to provide a process that overcomes the disadvantages of the known art.

SUMMARY

According to one aspect, the present subject matter provides a process for preparing 2-[[[1-(4-chlorophenyl)-1H-pyrazol-3-yl]oxy]methyl]-N-hydroxy-benzenamine of formula (I)

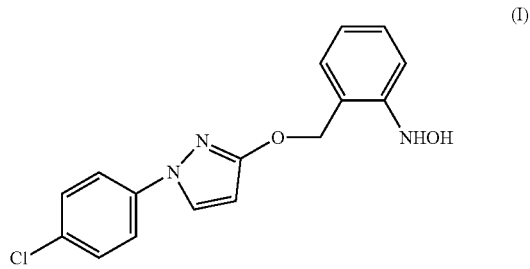

by mixing 1-(4-chlorophenyl)-3-[(2-nitrophenyl)methoxy]-1H-pyrazole of formula (II)

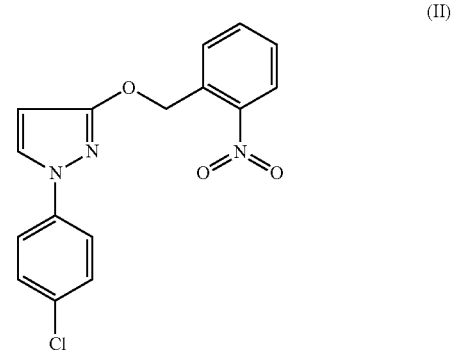 [SMILES: O=[N+]([O-])c1ccccc1COc1ccn(-c2ccc(Cl)cc2)n1]

with a nitrogen-containing base, a sulfur compound, a solvent and a platinum-based catalyst in the presence of hydrogen.

According to an embodiment, the nitrogen-containing base refers but not limited to ammonium hydroxide, tetramethyl ethylenediamine, triethyl amine and dimethylaniline. The sulfur compound refers but not limited to sulfides such as alkyl sulfides, dialkyl disulfides, aryl alkyl sulfides and hydrogen sulfide and sulfoxides such as dialkyl sulfoxides and aryl alkyl sulfoxides. In a specific embodiment, the sulfur compound comprises dimethyl sulfoxide. The solvent may be (i) a polar aprotic solvent, polar protic solvent, a non-polar solvent or a combination thereof. A polar aprotic solvent refers but not limited to methyl tert-butyl ether, acetonitrile, tetrahydrofuran, methyl iso-butyl ketone, and isopropylacetate. A polar protic solvent refers but not limited to water, ethanol, isopropanol. A non-polar solvent refers but not limited to toluene, hexane, xylene.

According to an embodiment, the molar ratio of the compound of formula (II) to the platinum-based catalyst is 1:1 to 2000:1. In a further embodiment, the molar ratio of the compound of formula (II) to the platinum-based catalyst is 500:1 to 1000:1. According to an embodiment, the molar ratio of the sulfur compound to the platinum-based catalyst is 100:1 to 350:1. The molar ratio of the nitrogen-containing base to the platinum-based catalyst is 75:1 to 225:1. The resulting compound of formula (I) may be present at a purity of at least 80%, at least 85%, at least 88%, at least 89%, at least 90%, at least 95%, at least 98%, or at least 99%.

In an embodiment, the process may further comprise the step of reacting the resulting compound of formula (I) with methylchloroformate in the presence of a base to give methyl 2-((1-(4-chlorophenyl)-1H-pyrazol-3-yloxy)methyl)phenyl(hydroxy)carbamate of formula (III).

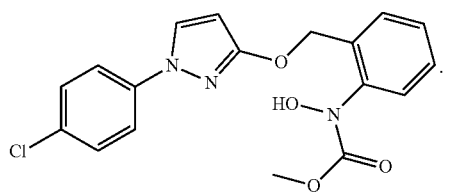
(III)

The base used in the preparation of the compound of formula (III) refers but not limited to sodium bicarbonate, sodium carbonate, potassium carbonate, potassium bicarbonate, sodium hydroxide, potassium hydroxide. The resulting compound of formula (III) may be present at a purity of at least 90%, at least 95%, at least 98%, or at least 99%.

According to another aspect, the present subject matter provides a process for preparing methyl 2-((1-(4-chlorophenyl)-1H-pyrazol-3-yloxy)methyl)phenyl(hydroxy)carbamate of formula (III)

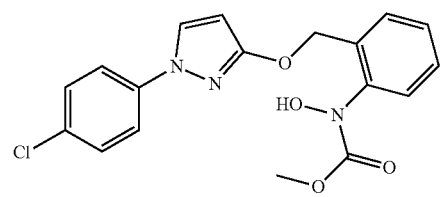
(III)

by mixing 1-(4-chlorophenyl)-3-[(2-nitrophenyl)methoxy]-1H-pyrazole of formula (II)

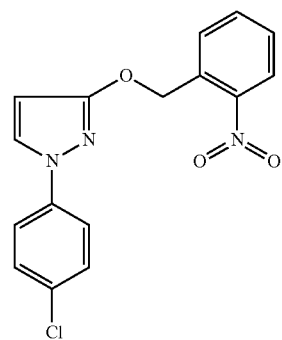
(II)

with a nitrogen-containing base, a sulfur compound, a solvent and a platinum-based catalyst in the presence of hydrogen to give 2-[[[1-(4-chlorophenyl)-1H-pyrazol-3-yl]oxy]methyl]-N-hydroxy-benzenamine of formula (I)

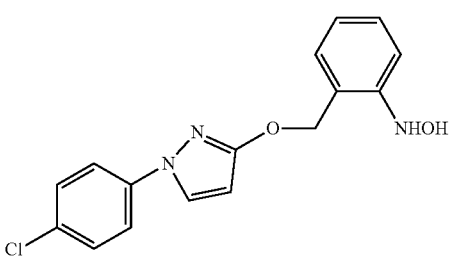
(I)

and subsequent reacting the resulting compound of formula (I) with methylchloroformate in the presence of a base. In an embodiment, the compound of formula (I) is not isolated prior to its reaction with methylchloroformate.

In an embodiment, the base used in the preparation of the compound of formula (III) refers but not limited to sodium bicarbonate, sodium carbonate, potassium carbonate, potassium bicarbonate, sodium hydroxide, potassium hydroxide. The resulting compound of formula (III) may be present at a purity of at least 90%, at least 95%, at least 98%, or at least 99%.

According to an embodiment, the nitrogen-containing base refers but not limited to ammonium hydroxide, tetramethyl ethylenediamine, triethyl amine and dimethylaniline. The sulfur compound refers but not limited to sulfides such as alkyl sulfides, dialkyl disulfides, aryl alkyl sulfides and hydrogen sulfide and sulfoxides such as dialkyl sulfoxides and aryl alkyl sulfoxides. In a specific embodiment, the sulfur compound comprises dimethyl sulfoxide. The solvent may be (i) a polar aprotic solvent, polar protic solvent, a non-polar solvent or a combination thereof. A polar aprotic solvent refers but not limited to methyl tert-butyl ether, acetonitrile, tetrahydrofuran, methyl iso-butyl ketone, and isopropylacetate. A polar protic solvent refers but not limited to water, ethanol, isopropanol. A non-polar solvent refers but not limited to toluene, hexane, xylene.

According to an embodiment, the molar ratio of the compound of formula (II) to the platinum-based catalyst is 1:1 to 2000:1. In a further embodiment, the molar ratio of the compound of formula (II) to the platinum-based catalyst is 500:1 to 1000:1. According to an embodiment, the molar ratio of the sulfur compound to the platinum-based catalyst is 100:1 to 350:1. The molar ratio of the nitrogen-containing base to the platinum-based catalyst is 75:1 to 225:1. The resulting compound of formula (I) may be present at a purity of at least 80%, at least 85%, at least 88%, at least 89%, at least 90%, at least 95%, at least 98%, or at least 99%.

In an embodiment, the herein described processes may be used in the production of pyraclostrobin.

DETAILED DESCRIPTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

As used herein, the term "mixture" or "combination" refers to, but is not limited to, a combination in any physical form, e.g., blend, solution, alloy, emulsion, or the like.

Throughout the application, descriptions of various embodiments use the term "comprising"; however, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, used of the term "about" herein specifically includes ±10% from the indicated values in the range. In addition, the endpoints of all ranges directed to the same component or property herein are inclusive of the endpoints, are independently combinable, and include all intermediate points and ranges.

Process for preparing 2-[[[1-(4-chlorophenyl)-1H-pyrazol-3-yl]oxy]methyl]-N-hydroxy-benzenamine The present subject matter provides an hydrogenation process for preparing 2-[[[1-(4-chlorophenyl)-1H-pyrazol-3-yl]oxy]methyl]-N-hydroxy-benzenamine of formula (I)

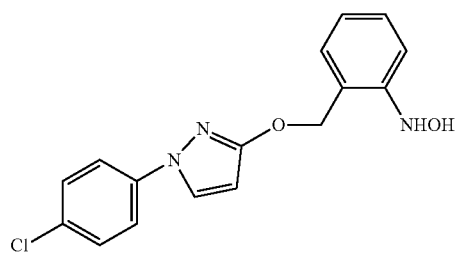

wherein the process comprises mixing 1-(4-chlorophenyl)-3-[(2-nitrophenyl)methoxy]-1H-pyrazole of formula (II)

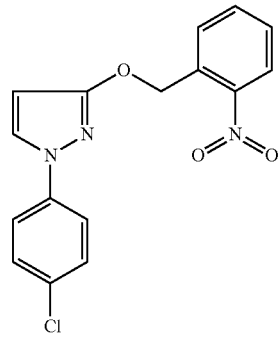

with a nitrogen-containing base, a sulfur compound, a solvent and a platinum-based catalyst in the presence of hydrogen.

The present process is advantageous in that the process is highly efficient, providing a short reaction time.

In another embodiment the present subject matter provides a process for preparing methyl 2-((1-(4-chlorophenyl)-1H-pyrazol-3-yloxy)methyl)phenyl(hydroxy)carbamate of formula (III) wherein the process comprises mixing 1-(4-chlorophenyl)-3-[(2-nitrophenyl)methoxy]-1H-pyrazole of formula (II) with a nitrogen-containing base, a sulfur compound, a solvent and a platinum-based catalyst in the presence of hydrogen to give 2-[[[1-(4-chlorophenyl)-1H-pyrazol-3-yl]oxy]methyl]-N-hydroxy-benzenamine of formula (I). The resulting compound of formula (I) is subsequently reacted with methylchloroformate in the presence of a base to form the compound of formula (III). According to an embodiment, the same solvent used in the step to prepare the compound of formula (I) may be used in the preparation of the compound of formula (III).

In an embodiment of the present process, the nitrogen-containing base, refers but not limited to ammonium hydroxide, tetramethyl ethylenediamine, triethyl amine and dimethylaniline. In a specific example, the nitrogen-containing base may be ammonium hydroxide.

In one embodiment, the sulfur compound, refers but not limited to sulfides and sulfoxides. According to some examples, sulfides may include alkyl sulfides, dialkyl disulfides, aryl alkyl sulfides and hydrogen sulfide; and sulfoxides may include dialkyl sulfoxides and aryl alkyl sulfoxides. In a specific embodiment, the sulfur compound may be dimethyl sulfoxide.

In an embodiment of the present processes, the solvent refers but not limited to methyl tert-butyl ether (MTBE), acetonitrile, tetrahydrofuran (THF), methyl iso-butyl ketone, ethanol, toluene and isopropylacetate. In a particular embodiment, the solvent may be a polar aprotic solvent selected from the group comprising methyl tert-butyl ether (MTBE), acetonitrile, tetrahydrofuran, methyl iso-butyl ketone, and isopropylacetate. In a specific embodiment, the solvent may be MTBE.

The platinum-based catalyst may be provided in metallic form on a carbon support at a concentration of approximately 1% to about 10% by weight platinum.

Alternatively, the platinum can be supplied on another carrier such as alumina, silica, barium sulfate, graphite, calcium carbonate, zirconium oxide or powdered supports.

In an embodiment of the present process, the compound of formula (II) is purified prior to mixing of compound of formula (II) with a nitrogen-containing base, a sulfur compound, a solvent and a platinum-based catalyst in the presence of hydrogen.

In a further embodiment of the present process, the compound of formula (II) is purified in the presence of a chelating agent. Chelating agent refers but not limited to Nitrilotriacetic acid (NTA), Ethylenediaminetetraacetic acid (EDTA), Diethylenetriaminepentaacetic acid (DTPA), Hydroxyethylethylenediaminetriacetic acid (HEDTA), Methylglycinediacetic acid (MGDA).

The ratio between the platinum-based catalyst and the different components of the reactions is also an important parameter in the processes of the present subject matter.

In an embodiment of the present processes, the molar ratio between the compound of formula (II) and the platinum-based catalyst is from about 1:1 to about 2000:1. In another embodiment, the molar ratio between the compound of formula (II) and the platinum-based catalyst is from about 500:1 to about 1000:1. In yet another embodiment, the molar ratio between the compound of formula (II) and the platinum-based catalyst is from about 900:1 to about 1000:1. In a further embodiment, the molar ratio between the compound of formula (II) and the platinum-based catalyst is from about 750:1 to about 1000:1. In a specific embodiment, the molar ratio between the compound of formula (II) and the platinum-based catalyst is about 969:1.

In an embodiment of the present processes, the molar ratio between the sulfur compound and the platinum-based catalyst is from about 1:1 to about 1000:1. In another embodiment, the molar ratio between the sulfur compound and the platinum-based catalyst is from about 1:1 to about 500:1. In yet another embodiment, the molar ratio between the sulfur compound and the platinum-based catalyst is from about 100:1 to about 350:1. In a further embodiment, the molar ratio between the sulfur compound and the platinum-based catalyst is from about 100:1 to about 200:1. In an even further embodiment, the molar ratio between the sulfur compound and the platinum-based catalyst is from about 100:1 to about 150:1. In a specific embodiment, the molar ratio between the sulfur compound and the platinum-based catalyst is about 125:1.

In an embodiment of the present processes, the molar ratio between the nitrogen-containing base and the platinum-based catalyst is from about 1:1 to about 1000:1. In another embodiment, the molar ratio between the nitrogen-containing base and the platinum-based catalyst is from about 1:1 to about 500:1. In yet another embodiment, the molar ratio between the nitrogen-containing base and the platinum-based catalyst is from about 50:1 to about 350:1. In a further embodiment, the molar ratio between the nitrogen-containing base and the platinum-based catalyst is from about 75:1 to about 225:1. In an even further embodiment, the molar ratio between the nitrogen-containing base and the platinum-based catalyst is from about 75:1 to about 150:1. In a specific embodiment, the molar ratio between the nitrogen-containing base and the platinum-based catalyst is about 125:1.

In an embodiment of the present processes, the ratio between the volume of solvent and the weight of the substrate (g) is from about 1:1 to about 25:1. In another embodiment the ratio between the volume of solvent and the weight of the substrate is from about 1:1 to about 20:1. In yet another embodiment, the ratio between the volume of solvent and the weight of the substrate is from about 5:1 to about 15:1.

In an embodiment of the present processes, the molar ratio between the nitrogen-containing base and the compound of formula (II) is from about 1:1 to about 1:50. In another embodiment, the molar ratio between nitrogen-containing base and the compound of formula (II) is from about 1:1 to about 1:25. In yet another embodiment, the molar ratio between nitrogen-containing base and the compound of formula (II) is from about 1:1 to about 1:10.

In an embodiment of the present processes, the molar ratio between the sulfur compound and the compound of formula (II) is from about 1:1 to about 1:50. In another embodiment, the molar ratio between the sulfur compound and the compound of formula (II) is from about 1:1 to about 1:25. In yet another embodiment, the molar ratio between the sulfur compound and the compound of formula (II) is from about 1:1 to about 1:10. In an even further embodiment, the molar ratio between the sulfur compound and the compound of formula (II) is from about 1:1 to about 1:10.

According to an embodiment, once the hydrogenation of 1-(4-chlorophenyl)-3-[(2-nitrophenyl)methoxy]-1H-pyrazole is complete and all the hydrogen present is consumed, the resultant product comprises the compound of formula (I) with a purity of at least 80%, at least 85%, at least 88%, at least 89%, at least 90%, at least 91%, at least 92%, at least 93%, at least 94%, at least 95%, at least 96%, at least 97%, at least 98%, or at least 99%.

In one embodiment, the hydrogenation of 1-(4-chlorophenyl)-3-[(2-nitrophenyl)methoxy]-1H-pyrazole is conducted at a temperature from about 15° C. to about 35° C., more preferably from about 20° C. to about 25° C.

In one embodiment, the hydrogenation of 1-(4-chlorophenyl)-3-[(2-nitrophenyl)methoxy]-1H-pyrazole is conducted at a pressure from about 1 bar to about 20 bar, more preferably from about 5 bar to about 15 bar.

Upon completion of the hydrogenation reaction, the resulting mixture may be filtered from the platinum-based catalyst. The catalyst may be cleaned and reused for a further hydrogenation reaction by washing the catalyst with the same solvent used in the hydrogenation reaction. As such, the catalyst may effortlessly be used in a subsequent hydrogenation process without further processing of the catalyst.

According to an embodiment, MTBE may be used in the hydrogenation reaction as well as to wash the catalyst from impurities. It was found that reusing the catalyst for further hydrogenation reactions had insignificant impact on the selectivity to produce the compound of formula (I). One may still achieve a purity of over approximately 90% when the catalyst is washed and reused two times, three times, four times or more.

According to an embodiment, it may be required to increase the amount of the nitrogen-containing base and/or the sulfur compound to the hydrogenation process when reusing the catalyst. The nitrogen-containing base and/or the sulfur compound may be increase by about 10%, 20%, 30%, 40%, 50% or more.

In certain embodiments, it may be necessary to add a small amount fresh catalyst to the hydrogenation process when reusing the catalyst. 10%, 20%, 30%, 40%, 50% or more of fresh catalyst may be added to the reused catalyst in each subsequent hydrogenation process. Therefore, the present process is advantageous in that it avoids the need for using a new expensive catalyst for each batch.

Process for Preparing methyl 2-((1-(4-chlorophenyl)-1H-pyrazol-3-yloxy)methyl)phenyl(hydroxy) carbamate In another embodiment the present subject matter provides a process for methyl 2-((1-(4-chlorophenyl)-1H-pyrazol-3-yloxy)methyl)phenyl(hydroxy)carbamate of formula (III)

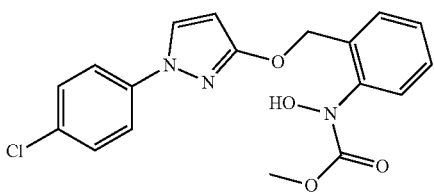

wherein the process comprises mixing 1-(4-chlorophenyl)-3-[(2-nitrophenyl)methoxy]-1H-pyrazole of formula (II)

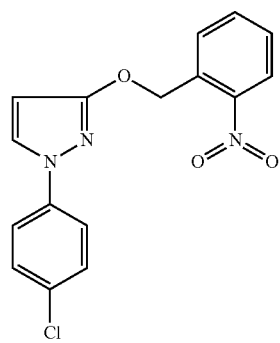

with a nitrogen-containing base, a sulfur compound, a solvent and a platinum-based catalyst in the presence of hydrogen to give 2-[[[1-(4-chlorophenyl)-1H-pyrazol-3-yl]oxy]methyl]-N-hydroxy-benzenamine of formula (I)

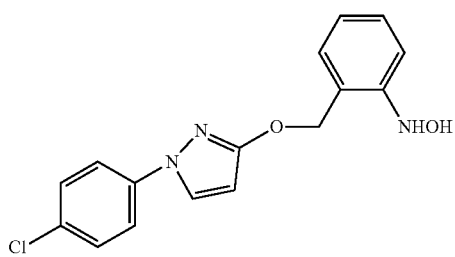

and subsequently reacting the resulting compound of formula (I) with methylchloroformate in the presence of a base. According to an embodiment, the compound of formula (I) is not isolated prior to its reaction with methylchloroformate. After the hydrogenation step, the catalyst may be washed with a solvent, and the resulting solution may immediately be used in the step of preparing 2-((1-(4-chlorophenyl)-1H-pyrazol-3-yloxy)methyl)phenyl(hydroxy)carbamate of formula (III).

According to an embodiment, the same solvent may be used from the first step of preparing 2-[[[1-(4-chlorophenyl)-1H-pyrazol-3-yl]oxy]methyl]-N-hydroxy-benzenamine of formula (I) through to the second step of preparing 2-((1-(4-chlorophenyl)-1H-pyrazol-3-yloxy)methyl)phenyl(hydroxy)carbamate of formula (III).

As such, the process described herein may be a one-pot process in which the resulting product of the hydrogenation step is directly used in the next step of producing 2-((1-(4-chlorophenyl)-1H-pyrazol-3-yloxy)methyl)phenyl(hydroxy)carbamate of formula (III).

In an embodiment of the present processes, the base is inorganic or organic base. Inorganic base refers to (i) carbonates, such as potassium carbonate or sodium carbonate; (ii) bicarbonates, such as potassium bicarbonate or sodium bicarbonate; (iii) hydroxides, such as sodium hydroxide or potassium hydroxide; (iv) alkali metal hydrides such as sodium hydride or potassium hydride; (v) alkali metal alcoholates, such as sodium methoxide or ethoxide or potassium tert-butoxide. Organic bases such as amines, e.g. triethylamine, pyridine or N, N-diethylaniline.

In another embodiment, the present subject matter provides a process for preparing 2-((1-(4-chlorophenyl)-1H-pyrazol-3-yloxy)methyl)phenyl(hydroxy)carbamate of formula (III) wherein the process comprises: mixing 1-(4-chlorophenyl)-3-[(2-nitrophenyl)methoxy]-1H-pyrazole of formula (II) with a nitrogen-containing base, a sulfur compound, a solvent and a platinum-based catalyst in the presence of hydrogen to give 2-[[[1-(4-chlorophenyl)-1H-pyrazol-3-yl]oxy]methyl]-N-hydroxy-benzenamine of formula (I) and subsequent reacting the resulting compound of formula (I) with methylchloroformate in the presence of a base in the same solvent used in the hydrogenation step; wherein the compound of formula (I) is not isolated prior to its reaction with methylchloroformate.

The present one-pot process reduces the cost of production, simplifies work-up, and minimizes any effluent disposal problems.

According to an embodiment, the resultant product comprises compound of formula (III) with a purity of at least 90%, at least 95%, at least 98%, or at least 99%.

The progress of the reaction can be monitored using any suitable method, which can include, for example, chromatographic methods such as, e.g., high performance liquid chromatography (HPLC), thin layer chromatography (TLC), and the like.

In yet another embodiment, the compound of formula (III) can be isolated from the reaction mixture by any conventional techniques well-known in the art. Such isolation techniques can be selected, without limitation, from the group consisting of concentration, extraction, precipitation, cooling, filtration, crystallization, centrifugation, and a combination thereof, followed by drying.

In yet another embodiment, the compound of formula (III) can be optionally purified by any conventional techniques well-known in the art. Such purification techniques can be selected, without limitation, from the group consisting of precipitation, crystallization, slurrying, washing in a suitable solvent, filtration through a packed-bed column, dissolution in an appropriate solvent, re-precipitation by addition of a second solvent in which the compound is insoluble, and a combination thereof.

The following examples illustrate the practice of the present subject matter in some of its embodiments, but should not be construed as limiting the scope of the present subject matter. Other embodiments will be apparent to one skilled in the art from consideration of the specification and examples. It is intended that the specification, including the examples, is considered exemplary only without limiting the scope and spirit of the present subject matter.

Purification Analysis:

Substrate purity was determined using quantitative HPLC analysis using external standards. Trace metal content was analyzed using ICP metal analysis for S and Fe.

EXAMPLE 1

Preparation of 2-[[[1-(4-chlorophenyl)-1H-pyrazol-3-yl]oxy]methyl]-N-hydroxy-benzenamine 1-(4-chlorophenyl)-3-[(2-nitrophenyl)methoxy]-1H-pyrazole of formula (II) is known from the literature or can be prepared by methods described therein (e.g. WO96/01256).

An exemplary experimental procedure is described as follows: 30 grams of 1-(4-chlorophenyl)-3-[(2-nitrophenyl) methoxy]-1H-pyrazole was dissolved in 190 grams of methyl tert-butyl ether (MTBE). This mixture was added to a 300 mL stirred-tank pressure reactor. 0.89 grams of dimethyl sulfoxide (DMSO) and 0.40 grams of 25% ammonium hydroxide was added to a 100 mL glass beaker and gently mixed. 0.633 grams of a platinum on activated charcoal hydrogenation catalyst (5% Pt basis) was placed in a second 100 mL glass beaker. The contents of both beakers were added to the reactor together with 33 grams of MTBE. The mixture was stirred mechanically at a temperature of 25° C. The catalyst surface was activated by purging the reactor three times with $N_2$, slowly evacuating the reactor and then purging twice with $H_2$. The reactor was evacuated in between each purge. The pressure of the reactor was set at 7 bar hydrogen and stirring was renewed at a speed of 730 rpm and a temperature of 25° C. As the pressure of the reactor dropped, hydrogen was added to the reactor in order to keep a constant pressure of 7 bar. Once no pressure drop was detected (i.e. the reaction is completed), the reactor was purged with $N_2$.

Purity of 2-[[[1-(4-chlorophenyl)-1H-pyrazol-3-yl]oxy] methyl]-N-hydroxy-benzenamine: 97.1%.

Preparation of 2-((1-(4-chlorophenyl)-1H-pyrazol-3-yloxy)methyl)phenyl(hydroxy)carbamate The reaction mixture was filtered through a Buchner funnel from the platinum on activated charcoal hydrogenation catalyst. The resulting solution was transferred to a 1 liter three bottle neck flask together with 150 mL of sodium carbonate (7.5% aqueous solution) and was stirred mechanically at room temperature. 8.6 grams of methylchloroformate (MCF) was added dropwise over a period of 0.5 hours. The mixture was then stirred for 80 minutes at 25° C. The solution was then filtered through sintered glass, and the solid residue was washed for 10 minutes with 150 mL of water and subsequently washed on the sintered glass with MTBE. The solid product was dried at in an oven at 80° C. for 12 hours.

Purity of 2-((1-(4-chlorophenyl)-1H-pyrazol-3-yloxy) methyl)phenyl(hydroxy)carbamate: 98.5%.

Overall yield of 2-((1-(4-chlorophenyl)-1H-pyrazol-3-yloxy)methyl)phenyl(hydroxy)carbamate: 88%.

EXAMPLE 2

Preparation of 2-[[[1-(4-chlorophenyl)-1H-pyrazol-3-yl]oxy]methyl]-N-hydroxy-benzenamine 1-(4-chlorophenyl)-3-[(2-nitrophenyl)methoxy]-1H-pyrazole of formula (II) is known from the literature or can be prepared by methods described therein (e.g. WO96/01256).

An exemplary experimental procedure is described as follows: 36 grams of 1-(4-chlorophenyl)-3-[(2-nitrophenyl) methoxy]-1H-pyrazole was dissolved in 100 grams of methyl tert-butyl ether (MTBE). This mixture was added to a 300 mL stirred-tank pressure reactor. 1.58 grams of dimethyl sulfoxide (DMSO) and 0.56 grams of 25% ammonium hydroxide was added to a 100 mL glass beaker and gently mixed. 0.633 grams of a platinum on activated charcoal hydrogenation catalyst (5% Pt basis) was placed in a second 100 mL glass beaker. The contents of both beakers were added to the reactor together with 33 grams of MTBE. The mixture was stirred mechanically at a temperature of 25° C. The catalyst surface was activated by purging the reactor three times with $N_2$, slowly evacuating the reactor and then purging twice with $H_2$. The reactor was evacuated in between each purge. The pressure of the reactor was set at 15 bar hydrogen and stirring was renewed at a speed of 730 rpm and a temperature of 25° C. As the pressure of the reactor dropped, hydrogen was added to the reactor in order to keep a constant pressure of 15 bar. Once no pressure drop was detected (i.e. the reaction is completed), the reactor was purged with $N_2$.

Purity of 2-[[[1-(4-chlorophenyl)-1H-pyrazol-3-yl]oxy] methyl]-N-hydroxy-benzenamine: 97.3%.

Preparation of 2-((1-(4-chlorophenyl)-1H-pyrazol-3-yloxy)methyl)phenyl(hydroxy)carbamate The reaction mixture was filtered through a Buchner funnel from the platinum on activated charcoal hydrogenation catalyst. The resulting solution was transferred to a 1 liter three bottle neck flask together with 150 mL of sodium carbonate (7.5% aqueous solution) and was stirred mechanically at room temperature. 11.3 grams of methylchloroformate (MCF) was added dropwise over a period of 0.5 hours. The mixture was then stirred for 80 minutes at 25° C. The solution was then filtered through sintered glass, and the solid residue was washed for 10 minutes with 150 mL of water and subsequently washed on the sintered glass with MTBE. The solid product was dried at in an oven at 80° C. for 12 hours.

Purity of 2-((1-(4-chlorophenyl)-1H-pyrazol-3-yloxy) methyl)phenyl(hydroxy)carbamate: 99.5%.

Overall yield of 2-((1-(4-chlorophenyl)-1H-pyrazol-3-yloxy)methyl)phenyl(hydroxy)carbamate: 91%.

General Procedure for the Purification of 1-(4-Chlorophenyl)-3-[(2-nitrophenyl)methoxy]-1H-pyrazole (II) from Metal Traces 1-(4-Chlorophenyl)-3-[(2-nitrophenyl)methoxy]-1H-pyrazole (50 g, 0.15 mol) was dissolved in MCB (250 gr, 5 weight equivalents) within a three necked 0.5 L flask equipped with a mechanical stirrer, a dropping funnel and a thermometer. The solution was stirred to homogenization at 70° C.

A solution of 4.5 M 3Na-EDTA (100 g, 5 weight equivalents) was slowly added dropwise after homogenization, keeping the temperature at 70° C. The biphasic mixture was stirred for an additional hour at 70° C. Ultimately, the mixture was cooled gradually to 15° C. during which a yellow solid precipitated.

The solid was filtered on sinter size 4 and transferred to a vacuum oven for an overnight drying at 70° C., 10 mbar.

As demonstrated in the above examples, a high yield of -((1-(4-chlorophenyl)-1H-pyrazol-3-yloxy)methyl)phenyl (hydroxy)carbamate may be produced using the selective hydrogenation process described hereinabove. The results demonstrate a high level of selectivity and efficiency of the reaction.

While the present subject matter has been shown and described with reference to preferred embodiments thereof, it will be understood by those skilled in the art that many alternatives, modifications and variations may be made thereto without departing from the spirit and scope thereof. Accordingly, it is intended to embrace all such alternatives, modifications, and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A process for preparing 2-[[[1-(4-chlorophenyl)-1H-pyrazol-3-yl]oxy]methyl]-N-hydroxy-benzenamine of formula (I)

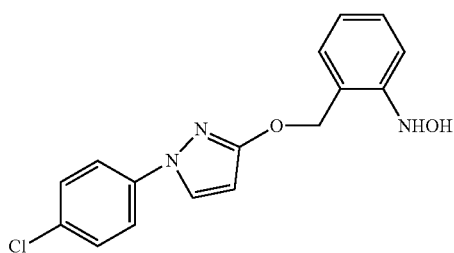

the process comprising:
mixing 1-(4-chlorophenyl)-3-[(2-nitrophenyl)methoxy]-1H-pyrazole of formula (II)

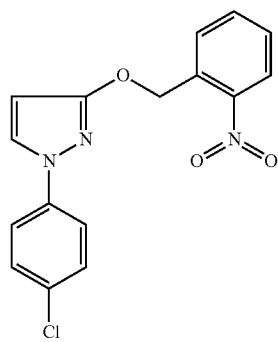

with a nitrogen-containing base, a sulfur compound, a solvent and a platinum-based catalyst in the presence of hydrogen, wherein the solvent is a polar aprotic solvent.

2. The process of claim 1, wherein the nitrogen-containing base is selected from the group consisting of ammonium hydroxide, tetramethyl ethylenediamine, triethyl amine, dimethylaniline or a combination thereof.

3. The process of claim 1, wherein the sulfur compound is sulfide, sulfoxide, or a combination thereof.

4. The process of claim 1, wherein the molar ratio of the compound of formula (II) to the platinum-based catalyst is 1:1 to 2000:1.

5. The process of claim 4, wherein the molar ratio of the sulfur compound to the platinum-based catalyst is 100:1 to 350:1.

6. The process of claim 5, wherein the molar ratio of the nitrogen-containing base to the platinum-based catalyst is 75:1 to 225:1.

7. The process of claim 1, wherein the resulting compound of formula (I) is present at a purity of at least 80%, at least 85%, at least 90%, at least 95%, at least 98%, or at least 99%.

8. A process for preparing methyl 2-((1-(4-chlorophenyl)-1H-pyrazol-3-yloxy)methyl)phenyl(hydroxy)carbamate of formula (III)

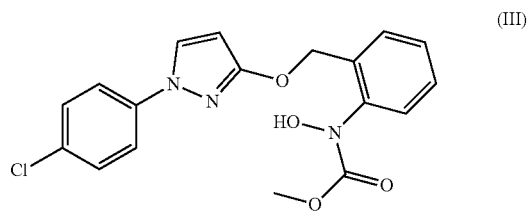 [SMILES: COC(=O)N(O)c1ccccc1COc1ccn(-c2ccc(Cl)cc2)n1]

the process comprising:
mixing 1-(4-chlorophenyl)-3-[(2-nitrophenyl)methoxy]-1H-pyrazole of formula (II)

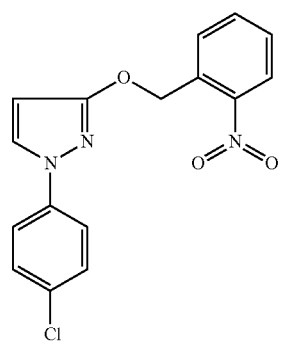

with a nitrogen-containing base, a sulfur compound, a solvent and a platinum-based catalyst in the presence of hydrogen, wherein the solvent is a polar aprotic solvent, to give 2-[[[1-(4-chlorophenyl)-1H-pyrazol-3-yl]oxy]methyl]-N-hydroxy-benzenamine of formula (I)

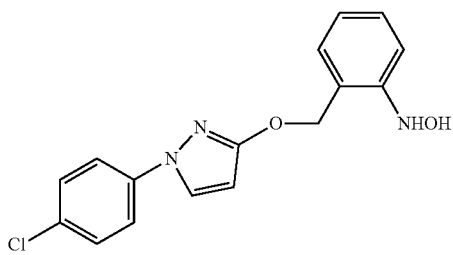

and subsequent reacting the resulting compound of formula (I) with methylchloroformate in the presence of a base.

9. The process of claim 8, wherein the compound of formula (III) is present at a purity of at least 90%, at least 95%, at least 98%, or at least 99%.

10. The process of claim 8, wherein the nitrogen-containing base is selected from the group consisting of ammonium hydroxide, tetramethyl ethylenediamine, triethyl amine, dimethylaniline or a combination thereof.

11. The process of claim 8, wherein the sulfur compound is a sulfide or a sulfoxide.

12. The process of claim 8, wherein the molar ratio of the compound of formula (II) to the platinum-based catalyst is 1:1 to 2000:1.

13. The process of claim 12, wherein the molar ratio of the sulfur compound to the platinum-based catalyst is 100:1 to 350:1.

14. The process of claim 13, wherein the molar ratio of the nitrogen-containing base to the platinum-based catalyst is 75:1 to 225:1.

15. The process of claim 8, wherein the compound of formula (I) is present at a purity of at least 80%, at least 85%, at least 90%, at least 95%, at least 98%, or at least 99%.

16. The process of claim 1, wherein the compound of formula (II) is purified prior to mixing the compound of formula (II) with said nitrogen-containing base, said sulfur compound, said solvent and said platinum-based catalyst in the presence of hydrogen.

17. A process of producing pyraclostrobin, using a compound of formula (I) prepared according to claim 1.

18. The process of claim 8, wherein the compound of formula (II) is purified prior to mixing the compound of formula (II) with said nitrogen-containing base, said sulfur compound, said solvent and said platinum-based catalyst in the presence of hydrogen.

* * * * *